United States Patent [19]

Tabei et al.

[11] Patent Number: 5,264,653
[45] Date of Patent: Nov. 23, 1993

[54] PROCESS FOR PURIFYING 1,1,3,4,4,6-HEXAMETHYLTETRALIN

[75] Inventors: Nobuaki Tabei, Yokohama; Hiroshi Sato, Niihama, both of Japan

[73] Assignee: Sumitomo Chemical Company, Limited, Osaka, Japan

[21] Appl. No.: 953,229

[22] Filed: Sep. 30, 1992

[30] Foreign Application Priority Data

Sep. 30, 1991 [JP] Japan ................. 3-251387

[51] Int. Cl.$^5$ ............................................. C07C 7/14
[52] U.S. Cl. ........................... 585/817; 585/812; 585/813; 585/815; 585/816
[58] Field of Search ............ 585/815, 816, 817, 812, 585/813

[56] References Cited

U.S. PATENT DOCUMENTS

| | | | |
|---|---|---|---|
| 3,856,875 | 12/1974 | Wood et al. | 260/668 F |
| 4,284,818 | 8/1981 | Sato et al. | 585/411 |
| 5,079,386 | 1/1992 | Meakins et al. | 585/409 |

FOREIGN PATENT DOCUMENTS 0393742  4/1990  European Pat. Off. .

OTHER PUBLICATIONS

Chem. Abstracts, vol. 97, No. 5, Aug. 2, 1982, Nitto Riken Industries, p. 545.

*Primary Examiner*—Anthony McFarlane
*Assistant Examiner*—Nhat D. Phan
*Attorney, Agent, or Firm*—Birch, Stewart, Kolasch & Birch

[57] ABSTRACT

A process for purifying 1,1,3,4,4,6-hexamethyltetralin is disclosed comprising melting crude 1,1,3,4,4,6-hexamethyltetralin in methanol with heating, cooling the resulting suspension, and adding seed crystals at a temperature of 45°-60° C.; as well as a process for purifying 1,1,3,4,4,6-hexamethyltetralin comprising recrystallizing crude 1,1,3,4,4,6-hexamethyltetralin from a mixed solvent of methanol and a solvent capable of easily dissolving 1,1,3,4,4,6-hexamethyltetralin, the proportion of this solvent being 10 to 25% by weight based on the weight of methanol. These processes make it possible to obtain 1,1,3,4,4,6-hexamethyltetralin of high purity easily with high recovery by purifying crude 1,1,3,4,4,6-hexamethyltetralin.

13 Claims, No Drawings

PROCESS FOR PURIFYING 1,1,3,4,4,6-HEXAMETHYLTETRALIN

BACKGROUND OF THE INVENTION

The present invention relates to a process for purifying 1,1,3,4,4,6-hexamethyltetralin (hereinafter referred to as HMT).

7-Acetyl-1,1,3,4,4,6-hexamethyltetralin obtained by acetylation of HMT is used as a perfume for soap and cosmetics.

Japanese Patent Examined Publication No. 53-10057 describes a process comprising producing HMT from p-cymene, removing a solvent ethylene dichloride by distillation at atmospheric pressure, recovering the excess p-cymene under reduced pressure, thereafter obtaining HMT as a colorless distillate (purity: 95%) having a boiling point of 80°-90° C. at a pressure of 1 mmHg, and then recrystallizing this HMT from an equal amount of isopropanol.

Japanese Patent Examined Publication No. 63-64410 describes a process comprising removing the solvent ethylene dichloride at atmospheric pressure, recovering the excess p-cymene under reduced pressure, thereafter obtaining crude HMT with a purity of 85.7%, and then recrystallizing the crude HMT from isopropanol.

However, in the conventional processes, the purity of purified HMT is not always high and the recovery is not sufficient, probably because isopropanol is a solvent capable of easily dissolving HMT and hence the amount of isopropanol used is limited.

SUMMARY OF THE INVENTION

In view of these circumstances, the present inventor earnestly investigated a process for purifying HMT, and consequently found that HMT of high purity can be obtained with high recovery by melting crude HMT in methanol, followed by crystallization by cooling, or recrystallizing crude HMT from a mixed solvent of methanol and a solvent capable of easily dissolving HMT.

An object of the present invention is to provide a process for purifying HMT to a high purity easily with high recovery.

Other objects and advantages of the present invention will become apparent from the following description.

According to the present invention, there is provided a process for purifying 1,1,3,4,4,6-hexamethyltetralin comprising melting crude 1,1,3,4,4,6-hexamethyltetralin in methanol with heating, cooling the resulting suspension, and adding seed crystals at a temperature of 45°-60° C. to carry out crystallization; or a process for purifying 1,1,3,4,4,6-hexamethyltetralin comprising recrystallizing crude 1,1,3,4,4,6-hexamethyltetralin from a mixed solvent of methanol and a solvent capable of easily dissolving 1,1,3,4,4,6-hexamethyltetralin, the proportion of this solvent being 10 to 20% by weight based on the weight of methanol.

DETAIL DESCRIPTION OF THE INVENTION

The crude HMT used in the present invention is not critical. There may be used, for example, HMT with a purity of about 85% obtained by removing starting materials and a solvent from a reaction mixture obtained by reacting p-cymene with 2,3-dimethyl-1-butene or neohexene, or HMT with a purity of about 95% obtained by distilling the HMT with a purity of about 85%.

HMT is difficultly soluble in methanol, but easily soluble in alcohols such as ethanol, isopropanol, n-propanol, n-butanol, etc.; ketones such as acetone, methyl ethyl ketone, isobutyl ketone, etc.; halogenated aliphatic hydrocarbons such as dichloromethane, chloroform, carbon tetrachloride, 1,1,1-trichloroethane, ethylene chloride, tetrachloroethylene, 1,2,3-trichloropropane, etc.; aromatic hydrocarbons such as benzene, toluene, xylene, trimethylbenzene, etc.; and halogenated aromatic hydrocarbons such as chlorobenzene, dichlorobenzene, etc.

In the process of the present invention using methanol alone as a solvent, methanol is used in a proportion of approximately 1.5-2 parts by weight per part by weight of crude HMT. When the amount of methanol used is below the above range, the purity of purified HMT is not high. Also when the amount is beyond the above range, the purity is not further improved in proportion to the amount of methanol. Crude HMT is mixed with methanol and then melted in methanol with heating to be suspended therein. In this case, just one small portion of HMT is dissolved.

Then, the suspension is slowly cooled. The cooling is conducted at a rate of 1° C. per approximately 1-10 minutes. The cooling is preferably slow because large crystals of high purity can be obtained. But, too slow cooling is not desirable. Seed crystals of HMT are added at a temperature of approximately 45°-60° C., preferably approximately 50°-55° C. When the temperature at the addition is too high, the seed crystals are dissolved. When the temperature is too low, HMT crystals are rapidly precipitated. Therefore, both of such temperatures are not desirable. The seed crystals are added in a proportion of approximately 0.1°-1% by weight based on the weight of the crude HMT. The powder of the seed crystals is usually used. When the seed crystals are not added or the amount of the seed crystals added is too small, HMT crystals are not sufficiently precipitated.

The suspension is cooled finally to approximately 0°-20° C. Although the final temperature is not critical, it is a temperature at which the precipitation of HMT crystals ceases substantially. The crystals precipitated are separated by filtration, centrifugation or the like. The crystals thus separated are preferably washed with methanol because crystals with higher purity can be obtained by the washing.

In the process comprising recrystallization from a mixed solvent, there is used a mixed solvent of methanol and any solvents capable of easily dissolving HMT, for example, alcohols such as ethanol, isopropanol, n-propanol, n-butanol, etc.; ketones such as acetone, methyl ethyl ketone, isobutyl ketone, etc.; halogenated aliphatic hydrocarbons such as dichloromethane, chloroform, carbon tetrachloride, 1,1,1-trichloroethane, ethylene chloride, tetrachloroethylene, 1,2,3-trichloropropane, etc.; aromatic hydrocarbons such as benzene, toluene, xylene, trimethylbenzene, etc.; and halogenated aromatic hydrocarbons such as chlorobenzene, dichlorobenzene, etc.

The solvent capable of easily dissolving HMT is used in a proportion of approximately 10-25% by weight based on the weight of methanol. When the amount is less than approximately 10%, it is difficult to dissolve HMT in the mixed solvent. Also, when the amount is more than approximately 25%, the recovery of HMT decrease. The mixed solvent is used in a proportion of approximately 1.5-2 parts by weight per part by weight of crude HMT, as in the case of using methanol alone. HMT and the mixed solvent are mixed and heated to dissolve HMT in the mixed solvent. Then, the resulting solution is cooled to precipitate HMT crystals. The cooling, seeding, etc. are carried out in the same manner as in the case of using methanol alone. Although the crystallization can be also carried out without seeding, it is preferably carried out by seeding because seeding facilitates the precipitation of crystals and their separation. After being separated, the HMT crystals can be improved in purity by washing with methanol or the mixed solvent containing methanol.

In the processes of the present invention, beautiful crystals ca be obtained by growing crystals with slow stirring, but too slow stirring results in settlement of crystals to the bottom of a vessel. Therefore, the crystallization by cooling is carried out while stirring at a slow rate at which crystals do not settle. Second recovery of crystals from a filtrate after the separation of crystals is difficult because the filtrate contains a large amount of tar. But, HMT of high purity can be recovered by applying the process of the present invention to a residue obtained by separating and recovering the tar by distillation. HMT with a purity of 99.9% or more can be obtained by practicing the process of the present invention repeatedly.

By the process of the present invention, 1,1,3,4,4,6-hexamethyltetralin can easily be purified to a high purity with high recovery.

DESCRIPTION OF THE PREFERRED EMBODIMENTS

EXAMPLES

The present invention is illustrated in detail with the following examples, which should not be construed as limiting the scope of the invention.

EXAMPLE 1

Into a 3-liter jacketed separable flask equipped with a stirrer and a condenser were charged 20.22 g of anhydrous aluminium chloride, 400.5 g of p-cymene and 300 g of cyclohexane, and vigorously stirred. Then, a mixture of 126 g of 2,3-dimethyl-1-butene, 156.9 g of t-butyl chloride and 300 g of cyclohexane was added dropwise to the resulting suspension over a period of 1.5 hours while maintaining the temperature of the suspension at 20° C., to carry out the reaction. The reaction mixture was stirred at the same temperature for another 10 minutes and then allowed to stand to separate tar, whereby an organic layer was obtained. The organic layer was washed successively with 600 g of water, 600 g of a 1% aqueous sodium hydroxide solution and 600 g of water. The solvent was removed from the organic layer by distillation at atmospheric pressure, after which the excess p-cymene was recovered under reduced pressure. Thus, 251.6 g of crude HMT with a purity of 86.0% was obtained.

In a 500-ml jacketed separable flask equipped with a stirrer and a condenser were placed 40.0 g of the HMT with a purity of 86.0% and 80 g of methanol. Then, the mixture in the flask was heated under reflux for 1 hour, after which the temperature of the mixture was reduced at a rate of 1° C. per 3 minutes. When the temperature became 55° C., 0.1 g of seed crystals of HMT were added. Subsequently, the temperature of the resulting mixture was reduced at a rate of 1° C. per 6 minutes. The mixture was stirred at 0° C. for 1 hour, after which the precipitate thus formed was filtered by suction through a Buchner funnel. After the filtration, the precipitate was washed with 20 g of methanol. In this case, the stirring was vigorously conducted so as to prevent HMT and the solvent from separating into two layers.

The crystals thus obtained were collected and the solvent was allowed to evaporate by means of a vacuum pump. The amount of the purified HMT thus obtained was 30.30 g, its purity 99.4%, and the recovery of HMT 87.7%.

The solvent was recovered from the filtrate, whereby 8.88 g of an oil was obtained. The HMT content of the oil was 48.1%.

EXAMPLE 2

In a 500-ml jacketed separable flask equipped with a stirrer and a condenser were placed 40.0 g cf HMT with a purity of 86.0%, 64 g of methanol and 16.0 g of ethanol. Then, the mixture in the flask was heated while refluxing methanol, to dissolve HMT. The temperature of the mixture was reduced at a rate of 1° C. per 3 minutes. When the temperature became 55° C., 0.1 g of seed crystals of HMT were added. Then, the temperature of the resulting mixture was reduced at a rate of 1° C. per 6 minutes. The reaction mixture was stirred at 0° C. for 1 hour, after which the precipitate thus formed was filtered by suction through a Buchner funnel. After the filtration, the precipitate was washed with 20 g of a mixed solvent of methanol and ethanol. During the above precipitation of crystals, the mixture was stirred at a slow rate at which crystals did not settle to the bottom of the flask.

The crystals thus obtained were collected and the solvent was allowed to evaporate by means of a vacuum pump. The amount of the purified HMT thus obtained was 30.86 g, its purity 99.1%, and the recovery of HMT 88.8%. The solvent was recovered from the filtrate, whereby 8.94 g of an oil was obtained. The HMT content of the oil was 45.6%.

EXAMPLE 3

The same procedure as in Example 2 was repeated except for stirring the mixture at such a rate at which crystals settled. The amount of the purified HMT thus obtained was 30.84 g, its purity 99.1%, and the recovery of HMT 88.8%. The solvent was recovered from the filtrate, whereby 9.25 g of an oil was obtained. The HMT content of the oil was 46.6%.

EXAMPLE 4

The same procedure as in Example 3 was repeated except for changing the temperature at the addition of seed crystals and the final temperature to 50° C. and 10° C., respectively. The amount of the purified HMT thus obtained was 31.25 g, its purity 99.2%, and the recovery of HMT 90.1%.

The solvent was recovered from the filtrate, whereby 9.05 g of an oil was obtained. The HMT content of the oil was 40.5%.

EXAMPLE 5

In a 500-ml jacketed separable flask equipped with a stirrer and a condenser were placed 40.0 g of HMT with a purity of 85.3% and 80 g of methanol. Then, the mixture in the flask was heated under reflux for 1 hour, after which the temperature of the mixture was reduced at a rate of 1° C. per 3 minutes. When the temperature became 55° C., 0.1 g of seed crystals of HMT were added. Subsequently, the temperature of the resulting mixture was reduced at a rate of 1° C. per 3 minutes. The mixture was stirred at 0° C. for 1 hour, after which the precipitate thus formed was filtered through a Buchner funnel. During the above precipitation of crystals, the mixture was stirred at a slow rate at which crystals did not settle to the bottom of the flask. The crystals thus obtained were collected and the solvent was allowed to evaporate by means of a vacuum pump. The amount of the purified HMT thus obtained was 31.55 g, its purity 96.5%, and the recovery of HMT 89.2%.

EXAMPLE 6

The same procedure as in Example 5 was repeated except for using a mixed solvent of 64 g of methanol and 16 g of ethanol in place of methanol and changing the final temperature to 5° C. The purity of the purified HMT thus obtained was 98.6%, and the recovery of HMT 88.5%.

EXAMPLE 7

The same procedure as in Example 5 was repeated except for using a mixed solvent of 48 g of methanol and 12 g of ethanol in place of methanol. The purity of the purified HMT thus obtained was 96.3%, and the recovery of HMT 87.0%.

EXAMPLE 8

The same procedure as in Example 5 was repeated except for using a mixed solvent of 72 g of methanol and 8 g of isopropanol in place of methanol. The purity of the purified HMT thus obtained was 96.6%, and the recovery of HMT 87.0%.

EXAMPLE 9

The same procedure as in Example 5 was repeated except for using a mixed solvent of 54 g of methanol and 6 g of isopropanol in place of methanol. The purity of the purified HMT thus obtained was 96.7%, and the recovery of HMT 89.3%.

EXAMPLE 10

The same procedure as in Example 5 was repeated except for using a mixed solvent of 72 g of methanol and 8 g of ethylene chloride in place of methanol. The purity of the purified HMT thus obtained was 97.8%, and the recovery of HMT 86.2%.

COMPARATIVE EXAMPLE 1

In a 500ml jacketed separable flask equipped with a stirrer and a condenser were placed 40.0 g of HMT with a purity of 86.0% and 23 g of isopropanol. The mixture in the flask was heated under reflux for 1 hour, after which the temperature of the mixture was reduced at a rate of 1° C. per 3 minutes. When the temperature became 50° C., 0.1 g of seed crystals of HMT were added. Then, the temperature of the resulting mixture was reduced at a rate of 1° C. per 3 minutes. The mixture was stirred at 5° C. for 1 hour, after which the precipitate formed was filtered by suction through a Buchner funnel. During the above precipitation of crystals, the mixture was stirred at such a rate at which crystals did not settle to the bottom of the flask. The crystals thus obtained were collected and the solvent was allowed to evaporate by means of a vacuum pump. The amount of the purified HMT thus obtained was 29.03 g, its purity 94.4%, and the recovery of HMT 80.3%.

What is claimed is:

1. A process for purifying 1,1,3,4,4,6-hexamethyltetralin comprising melting crude 1,1,3,4,4,6-hexamethyltetralin in methanol with heating, cooling the resulting suspension, adding seed crystals of 1,1,3,4,4,6-hexamethyltetralin to said cooled suspension at a temperature of 45°–60° C. and cooling the resulting mixture to obtain crystals of 1,1,3,4,4,6-hexamethyltetralin.

2. The process for purifying 1,1,3,4,4,6-hexamethyltetralin according to claim 1 which further comprises separating the crystals and then washing the crystals with methanol.

3. The process for purifying 1,1,3,4,4,6-hexamethyltetralin according to claim 1, wherein the cooling is conducted at a rate of 1° C. per 1 to 10 minutes.

4. The process for purifying 1,1,3,4,4,6-hexamethyltetralin according to claim 1 or 3, wherein the cooling of the mixture is effected until the temperature of the mixture is 0–20° C.

5. The process for purifying 1,1,3,4,4,6-hexamethyltetralin according to claim 1, wherein said methanol is present in an amount of 1.5 to 2 parts by weight per part by weight of crude 1,1,3,4,4,6-hexamethyltetralin.

6. A process for purifying 1,1,3,4,4,6-hexamethyltetralin comprising recrystallizing crude 1,1,3,4,4,6-hexamethyltetralin from a solution mixture of methanol and a solvent capable of dissolving 1,1,3,4,4,6-hexamethyltetralin, said solvent being present in an amount of 10 to 25% by weight based on the weight of methanol to obtain crystals of 1,1,3,4,4,6-hexamethyltetralin.

7. The process of purifying 1,1,3,4,4,6-hexamethyltetralin according to claim 6, wherein the recrystallizing is effected by dissolving 1,1,3,4,4,6-hexamethyltetralin in the solution mixture of methanol and a solvent capable of dissolving 1,1,3,4,4,6-hexamethyltetralin with heating, cooling the solution, adding seed crystals of 1,1,3,4,4,6-hexamethyltetralin to the cooled solution at a temperature of 45°–60° C. and then cooling the resulting mixture.

8. The process for purifying 1,1,3,4,4,6-hexamethyltetralin according to claim 6 or 7, wherein cooling for the recrystallization is conducted at a rate of 1° C. per 1 to 10 minutes.

9. The process for purifying 1,1,3,4,4,6-hexamethyltetralin according to claim 6 or 7, which further comprises separating the crystals of 1,1,3,4,4,6-hexamethyltetralin and then washing the crystals with a solvent mixture containing methanol.

10. The process for purifying 1,1,3,4,4,6-hexamethyltetralin according to claim 6, wherein the solvent capable of dissolving 1,1,3,4,4,6-hexamethyltetralin is at least one compound selected from the group consisting of ethanol, propanol, butanol, acetone, methyl ethyl ketone, methyl isobutyl ketone, dichloromethane, chloroform, carbon tetrachloride, 1,1,1-trichloroethane, ethylene chloride, tetrachloroethylene, 1,2,3-trichloropropane, benzene, toluene, xylene, chlorobenzene and dichlorobenzene.

11. The process for purifying 1,1,3,4,4,6-hexamethyltetralin according to claim 6, wherein said solution mixture is present in an amount of 1.5 to 2 parts by weight per part by weight of crude 1,1,3,4,4,6-hexamethyltetralin.

12. The process for purifying 1,1,3,4,4,6-hexamethyltetralin according to claim 1 or 7 wherein the seed crystals are added at a temperature of 50-55° C.

13. The process for purifying 1,1,3,4,4,6-hexamethyltetralin according to claim 1 or 7, wherein the seed crystals are added in a proportion of 0.1 to 1% by weight based on the weight of crude 1,1,3,4,4,6-hexamethyltetralin.

* * * * *